United States Patent [19]

Ou

[11] Patent Number: 5,636,645

[45] Date of Patent: Jun. 10, 1997

[54] METHOD AND SURGICAL GLOVE FOR PERFORMING LAPAROSCOPIC-ASSISTED MINI LAPAROTOMY

[76] Inventor: Honzen Ou, 2682 Shadow Canyon Dr., Diamond Bar, Calif. 91765

[21] Appl. No.: 395,446

[22] Filed: Feb. 28, 1995

[51] Int. Cl.$^6$ .................................................. A61B 19/00
[52] U.S. Cl. .................................................. 128/898
[58] Field of Search .................... 128/897–98; 2/159, 2/160, 161.7

[56] References Cited

U.S. PATENT DOCUMENTS

| | | | |
|---|---|---|---|
| 3,992,723 | 11/1976 | Lazanas | 2/161 R |
| 4,773,902 | 9/1988 | Lentz et al. | 604/265 |
| 5,020,160 | 6/1991 | Cano | 2/159 |
| 5,024,852 | 6/1991 | Busnel et al. | 427/2 |
| 5,025,502 | 6/1991 | Raymond et al. | 2/159 |
| 5,236,703 | 8/1993 | Usala | 424/78.36 |
| 5,309,573 | 5/1994 | Solar et al. | 2/160 |

FOREIGN PATENT DOCUMENTS

| | | |
|---|---|---|
| 0003720 | 10/1955 | Germany . |
| 1526635 | 7/1989 | U.S.S.R. . |

Primary Examiner—Angela D. Sykes
Assistant Examiner—John P. Lacyk
Attorney, Agent, or Firm—David A. Farah; Sheldon & Mak, Inc.

[57] ABSTRACT

A method of performing surgery incorporating the advantages of manual palpation manipulation and dissection with the advantages of laparoscopy. The method comprises making a first opening in a body cavity wall to permit entry of a surgeon's gloved hand. Next, the surgeon's gloved hand is placed into the body cavity through the opening and a gas infused into the body cavity through the first opening or through a second opening. The surgical procedure is performed and the surgeon's hand is removed from the body cavity. The surgeon's gloved hand can be provided with a sealant for engaging the sides or surrounding tissue of the first opening, thereby creating a substantially gas-tight seal. The sealant can comprise an inflatable member circumferentially disposed around the forearm portion of the surgeon's glove or can comprise a disk having an adhesive on the distal surface for sealingly engaging the surrounding tissue of an opening in a body cavity wall. Both the inflatable member and the disk can have a central flange disposed within the central opening of the inflatable member or disk. The flange has a central opening for permitting entry of the surgeon's gloved forearm. The flange can be affixed to the forearm portion of the surgeon's glove through its central opening or can be detachable.

19 Claims, 3 Drawing Sheets

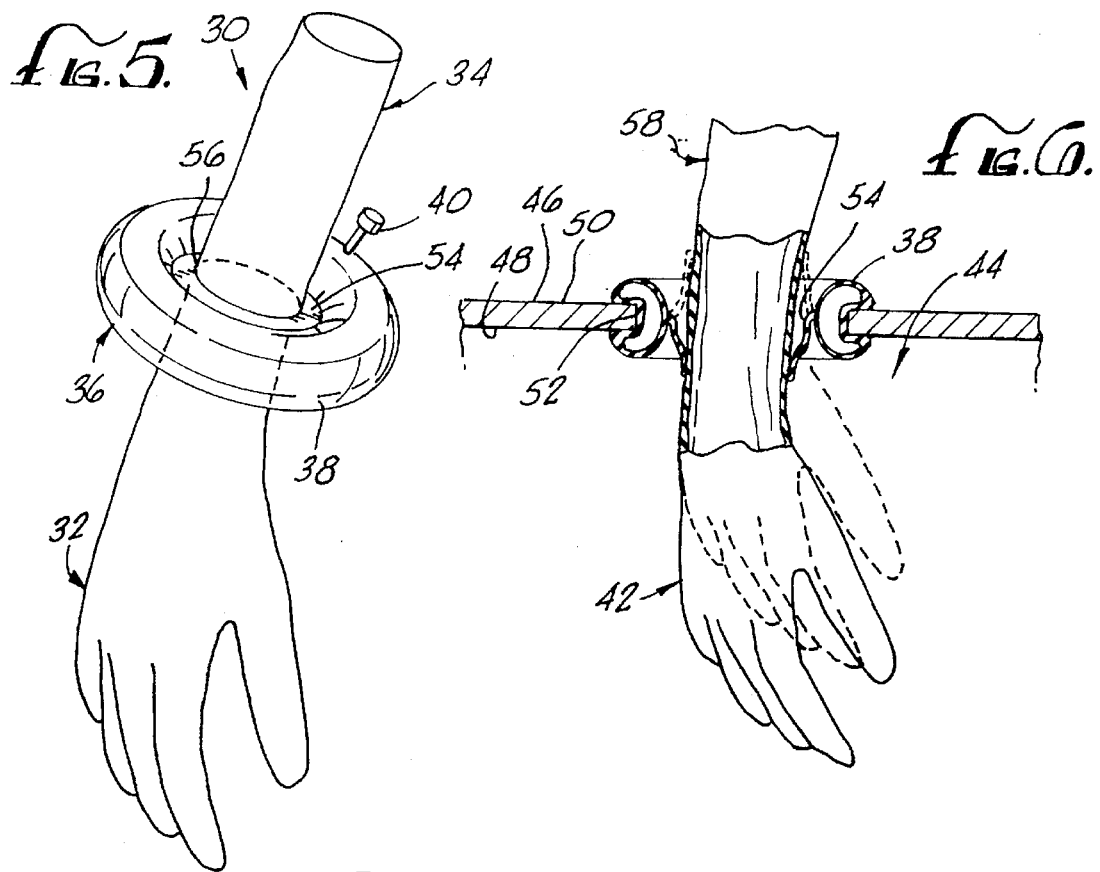
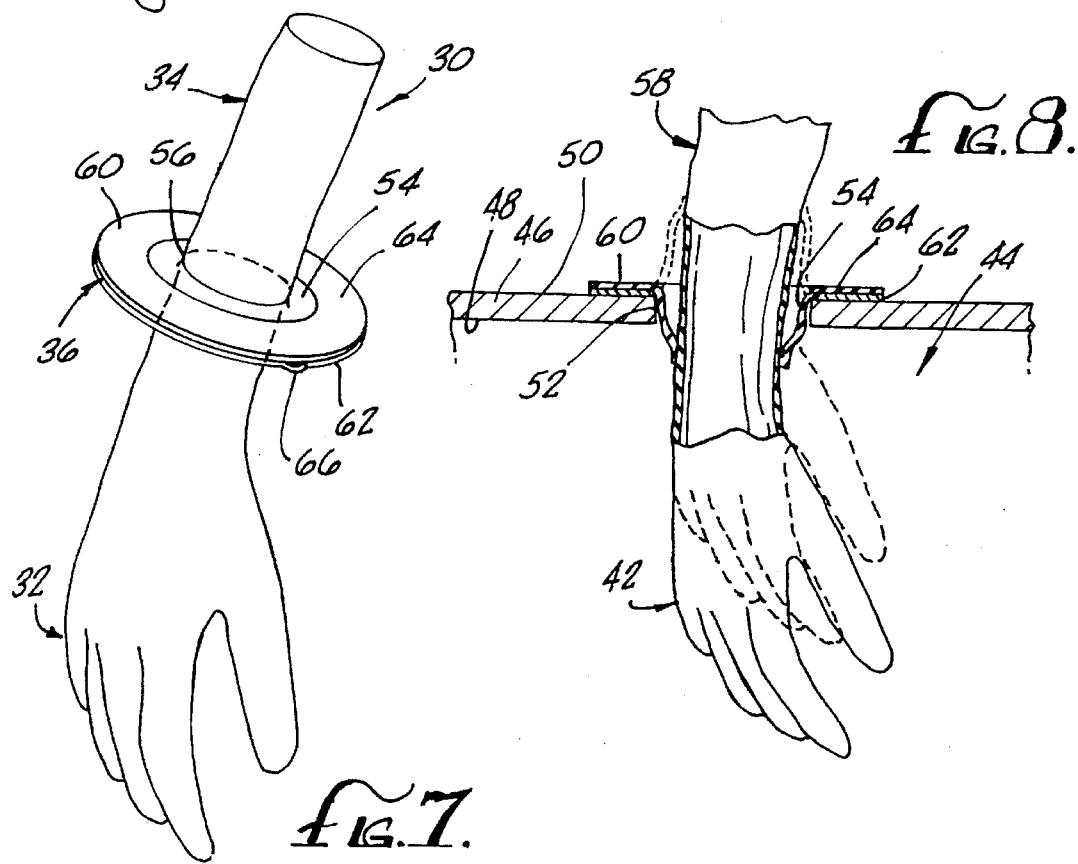

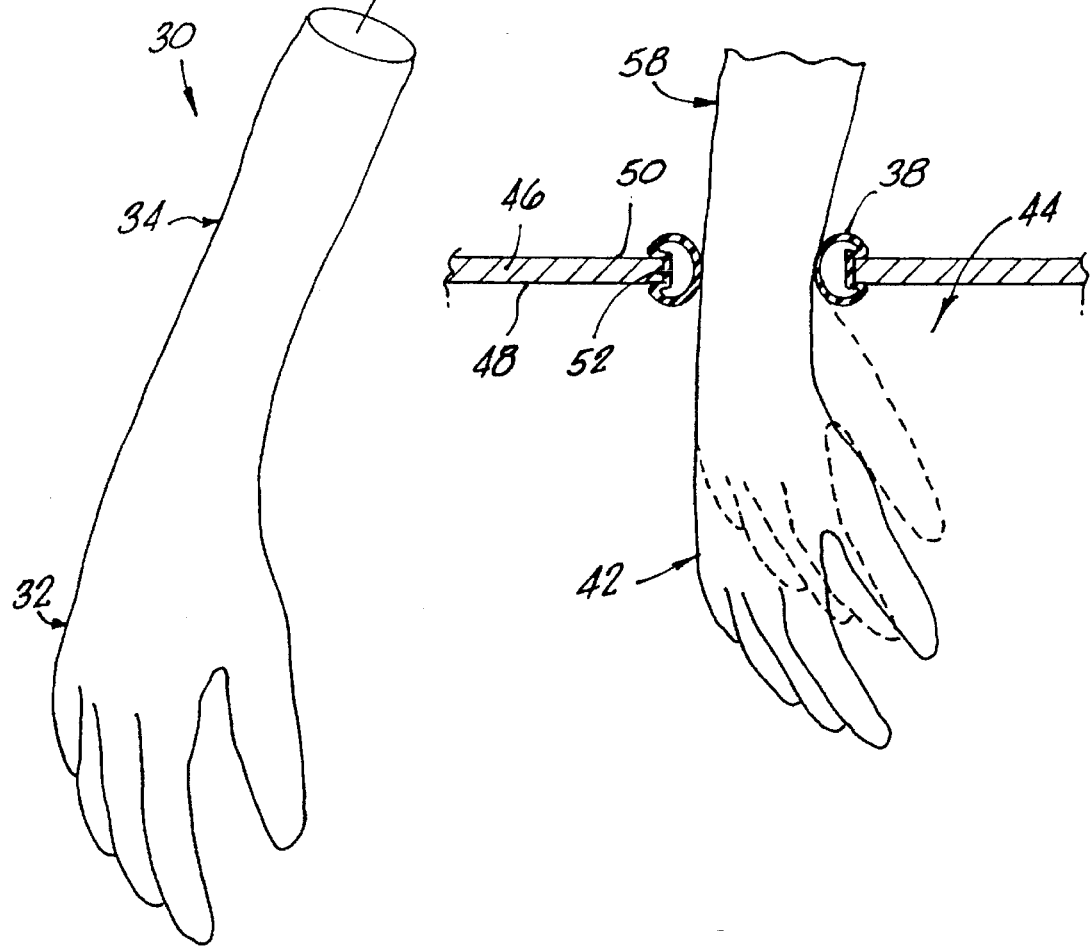

METHOD AND SURGICAL GLOVE FOR PERFORMING LAPAROSCOPIC-ASSISTED MINI LAPAROTOMY

BACKGROUND

Many diseases and conditions of humans and animals require surgical treatment. In recent years, some types of surgery previously utilizing a large incision into a body cavity wall have been supplanted by laparoscopic techniques which utilize several small openings into the body cavity wall. In these types of surgery, laparoscopic techniques have decreased the length of inpatient hospital stays, improved post-surgical cosmetic results, and in many cases have decreased morbidity and mortality, thereby saving costs.

Certain technically complex surgical procedures such as subtotal colectomy, however, are difficult to perform laparoscopically. In traditional, non-laparoscopic surgery, the technical requirements of these procedures were accomplished in part by surgeons using their hands directly to palpate lesions in order to determine the extent of the necessary dissection, and to manipulate and dissect tissue accurately within the body cavity.

Conventional laparoscopic surgery, however, excludes direct manual palpation, manipulation and dissection by the surgeon. For some procedures such as cholecystectomy, this exclusion may not be significantly disadvantageous. For other procedures such as subtotal colectomy, however, the lack of direct manual palpation, manipulation and dissection renders the surgery difficult to perform laparoscopically, and is therefore a cause of continued resistance to performing these procedures laparoscopically.

It would, therefore, be advantageous to have a method of performing these complex surgeries in a body cavity which incorporate the advantages of laparoscopic techniques with the advantages of direct manual palpation, manipulation and dissection. Further, it would be advantageous to have a device which would permit the surgeon to use direct manual skills with conventional laparoscopic techniques, to obtain the benefits of both in one surgical procedure.

SUMMARY

The present invention is directed to a method of performing surgery and a device that allows the surgery to be performed practically, thereby satisfying these needs. According to one embodiment, the present invention is a method for performing surgery. The method involves making a first opening in a body cavity wall of sufficient dimensions to permit entry of the surgeon's gloved hand into the body cavity. Next, the surgeon's gloved hand is placed into the body cavity through the first opening. A suitable gas is infused into the body cavity through the first opening, or through a second opening in the body cavity wall. The surgical procedure is then performed and the surgeon's hand removed from the body cavity.

The method of performing surgery according to the present invention further comprises providing a surgical glove having a hand portion, a forearm portion attached to the hand portion, and a sealant. The sealant can be used to seal the forearm portion of the glove to the sides or surrounding tissue of an opening in the body cavity wall. Once the surgeon's gloved hand has been placed into the body cavity through an opening in the body cavity wall, the sealant is used to engage to actuate the sides or surrounding tissue of the opening, thereby creating a substantially gas-tight seal between the sides of the opening and the forearm portion of the surgeon's gloved forearm.

The sealant can comprise an inflatable member having a central opening for permitting entry of the gloved surgeon's hand therethrough, and can have an inflation mechanism for inflating the inflatable member. The sealant can further comprise a flange having a central opening, disposed within the central opening of the inflatable member. The flange can be affixed to the forearm portion of the surgical glove or can be detachable therefrom.

The sealant can also comprise a disk with a central opening having a proximal surface and a distal surface, the distal surface has an adhesive thereon. The sealant can further comprise a flange having a central opening disposed within the central opening of the disc. The flange can be affixed to the forearm portion of the surgical glove or can be detachable therefrom.

FIGURES

The features, aspects and advantages of the present invention will become better understood with regard to the following description, appended claims and accompanying figures where:

FIG. 5 is a perspective view of another surgical glove having features of the invention;

FIG. 6 is an environmental view of the surgical glove shown in FIG. 5 being used in surgery according to one embodiment of the present invention;

FIG. 7 is a perspective view of another surgical glove having features of the invention;

FIG. 8 is an environmental view of the surgical glove shown in FIG. 7 being used in surgery according to one embodiment of the present invention;

FIG. 9 is a perspective view of another surgical glove having features of the invention;

FIG. 10 is an environmental view of the surgical glove shown in FIG. 9 being used in surgery according to one embodiment of the present invention.

DESCRIPTION

In one embodiment of the present invention, there is provided a method of performing surgery which combines the advantages of laparoscopic surgery with the advantages of direct manual palpation, manipulation and dissection by the surgeon as in traditional non-laparoscopic surgery. The method of performing surgery according to this embodiment of the present invention is designated herein as "laparoscopic-assisted mini laparotomy" (LHL). While the designation "laparotomy" is used with respect to this method, it will be understood by those with skill in the art that the method can be adapted for surgeries in body cavities other than the abdomen, as well as to animals other than humans.

Figures 1, 2:
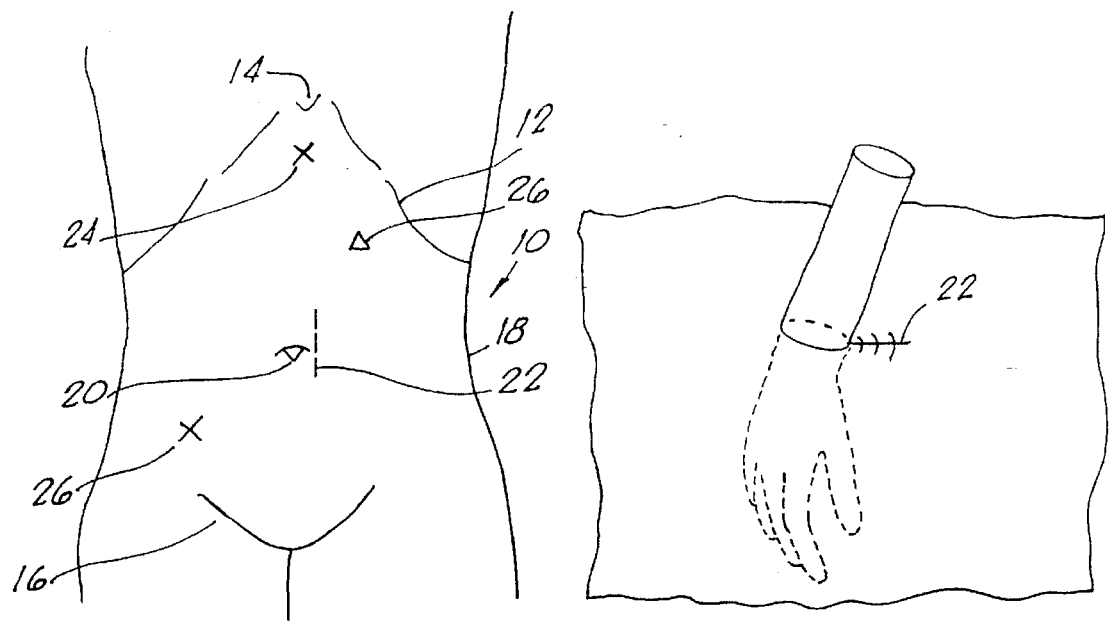
FIG. 1 is a diagram of an anterior abdominal wall showing the location of certain openings used in the method of performing surgery according to one embodiment of the present invention.
FIG. 2 is a top perspective view of a method according to the present invention.

Referring now to FIG. 1, there is illustrated a diagram of an anterior abdominal wall 10 showing the location of openings made for LHL according to one embodiment of the present invention. As shown, the anterior abdominal wall 10 is bounded by the lower margin of the rib cage 12 and xiphoid process 14 superiorly, the region of the inguinal ligaments 16 inferiorly, and the flanks 18 laterally. The umbilicus 20 is indicated centrally.

One method of performing LML according to the present invention is as follows. First, a patient having an appropriate disease or condition amenable to surgical treatment is prepped in a manner known to those with skill in the art. Next, two openings are made in the anterior abdominal wall 10. The location of the two openings depends on the specific procedure to be performed, the handedness of the surgeon and the body habitus of the patient. The choice of the exact location of the incision will be understood by those with skill in the art with reference to the disclosure herein.

A first of the two openings 22 is made in dimensions large enough to permit passage of the surgeon's gloved hand and at least part of the surgeon's gloved forearm into the abdominal cavity. In one embodiment, the dimensions of the first opening 22 are merely large enough to permit passage of the surgeon's gloved hand and part of the surgeon's gloved forearm, such that the surgeon's gloved forearm substantially encounters the sides of the first opening 22, thereby creating a seal between the sides of the first opening 22 and the surgeon's gloved forearm. Such a first opening 22 is particularly possible where the patient has considerable subcutaneous adipose tissue because the tissue will tend to close around the surgeon's gloved forearm rather than retract away as the more elastic dermis will tend to do. In this embodiment, the first opening 22 can be made initially smaller than necessary and enlarged to the proper size determined by attempting to pass the surgeon's gloved forearm into the first opening 22.

In another embodiment, the first opening 22 is initially made slightly larger than necessary to merely permit passage of the surgeon's gloved hand and part of the surgeon's gloved forearm. In this embodiment, it is necessary to close the sides of the first opening 22 around the surgeon's gloved forearm to create a seal or to use a sealant to create a seal between the surgeon's gloved forearm and the sides of the first opening 22. The exact dimensions of the first opening 22 according to this embodiment will depend partly on the size of the surgeon's gloved hand and forearm and partly on the mechanism of sealing or sealant used. For illustrative purposes only, a conventional abdominal wall incision approximately 4 cm to 8 cm is a suitable first opening 22 for a surgeon having a glove size of approximately 7. In a preferred embodiment, the incision is approximately 5 cm for a surgeon having a glove size of approximately 7. The length of this incision can initially be made on the short side and can be expanded to permit full entry of the surgeon's gloved hand and part of his forearm.

The purpose of this first opening 22 is to permit entry of the surgeon's gloved hand and performance of the procedure, while keeping disruption of the tissues of the anterior abdominal wall 10 to a minimum. Keeping tissue disruption to a minimum, advantageously decreases the length of inpatient hospital stays, improves post-surgical cosmetic results, and can decrease morbidity compared to traditional open laparotomy. Therefore, large incisions such as a midline incision extending from the xiphoid process 14 to the umbilicus or from the umbilicus to the pubic symphysis are inappropriate for LML.

A second of the two openings 24 is made in the anterior abdominal wall 10 in a manner and position to permit infusion of gas under pressure into the abdomen. This second opening 24 can be made before or after the first opening 22. If the second opening 24 is made after the first opening 22, the surgeon's gloved hand can be introduced through the first opening 22 and can be used to assist placement of the second opening 24, such as by a trocar.

Next, the sides of the first opening 22 are closed around the surgeon's gloved forearm using sutures, as shown in FIG. 2, or a sealant is employed, with or without sutures, to create a substantially gas-tight seal between the surgeon's gloved forearm and the sides of the first opening 22. This is preferably done once the second opening 24 is made though it can be done before the second opening 24 is made. The sealant can be one or more appropriate means, such as surgical clips, and can include the specialized devices disclosed herein.

For example, the sides of the first opening 22 can be closed around the surgeon's gloved forearm by using sutures in a purse-string configuration around the sides of the first opening 22 and than putting the sutures under tension to seal the first opening 22 to the surgeon's gloved forearm. Purse-string sutures advantageously allow adjustment of the size of the first opening 22 to permit entry or withdrawal of part of the surgeon's gloved forearm into the body cavity while maintaining the surgeon's gloved hand within the cavity. Alternately, interrupted or running sutures, including figure-of-eights, can be passed through the dermis and/or subcutaneous tissues surrounding the first opening 22 to create the seal. Preferably, these sutures are tied in a manner such that they can be adjusted to enlarge or narrow the first opening 22, without removing the sutures. This can be accomplished by techniques well known in the surgical arts.

Next, a suitable gas is infused into the abdominal cavity under pressure. Preferably, the gas is infused through the second opening 24. In one preferred embodiment, the gas is substantially pure carbon dioxide. Other gases and mixtures of gases are suitable, however. The choice of the type of gas and pressure will be understood by those with skill in the art with reference to the disclosure herein.

The closed sides of the first opening 22 or the sealant sealing the sides of the first opening 22 to the surgeon's gloved forearm substantially prevents leakage of the gas through the first opening 22. Before infusion of the gas, or more preferably after infusion of the gas, additional openings 26 are made in the anterior abdominal wall 10 for passage of a laparoscope and other laparoscopic instruments necessary to perform the procedure.

After the openings are made in the anterior abdominal wall 10, the surgeon's hand introduced, the gas infused, and instruments placed into the anterior abdominal wall 10, the surgical procedure is performed. At an appropriate point in the procedure, such as at the completion of the procedure, the sutures closing the sides of the first opening 22 against the surgeon's gloved forearm or the sealant closing the area between the sides of the first opening 22 and the surgeon's gloved forearm are removed or deactuated. This allows gas remaining in the abdominal cavity to be expelled, if it has not already been expelled through one of the other abdominal wall openings 26. Then, the surgeon's gloved hand is removed from the abdominal cavity. The first opening 22 is closed in a conventional manner.

It will be understood by those with skill in the art that, depending on the procedure, the sutures closing the sides of the first opening 22 to surgeon's gloved forearm or the sealant can be removed or deactuated to allow removal of the surgeon's hand from the abdominal cavity during the procedure. In this case, the first opening 22 can be closed and the surgical procedure completed laparoscopically, or, where appropriate, the surgeon's gloved hand can be reintroduced into the abdominal cavity to complete the surgical procedure. If the reintroduction of gas into the abdominal cavity is necessary, steps equivalent to the steps for initial insertion of the surgeon's gloved hand and forearm and infusion of gas are employed.

For example, in a subtotal colectomy using LML, the bowel can be pulled through the first opening 22 for extracorporeal resection and anastomosis, and then replaced into the abdominal cavity. If needed, the surgeon's gloved hand and part of his forearm can be reinsorted through the first opening 22 and the sides of the first opening 22 resutured or the sealant reattached or reactuated, if necessary to allow infusion of additional gas into the abdominal cavity, and thereby allow completion of the procedure.

It will be apparent to those with skill in the art, that the method of performing LML disclosed herein can be used for a variety of intraabdominal procedures. For example, suitable procedures include subtotal or total colectomy, splenectomy, prostatectomy, hepatectomy, pancreatectomy, nephrectomy, gastrectomy, as well as abdominal exploration, cholecystectomy, esophageal or diaphragmatic surgery, or other procedures as would be understood by those with skill in the art with reference to the disclosure herein.

According to another aspect of the present invention, there is provided a surgical glove in combination with a sealant suitable for use in performing the method of LML according to one embodiment of the present invention. The glove and sealant are used to allow introduction of the gloved surgeon's hand and part of his gloved forearm through an opening in a body cavity wall, thereafter sealing the area between the sides of the opening and the gloved surgeon's forearm utilizing the sealant.

Referring now to FIGS. 3 through 10, there is illustrated a surgical glove with sealant according to one aspect of the present invention. The surgical glove 30 comprises a hand portion 32 and forearm portion 34 affixed to the hand portion 32. The hand portion 32 and forearm portion 34 comprise substantially elastic, flexible material which allows insertion of the surgeon's hand and forearm into the glove 30, the surgeon's forearm being bare or being covered in whole or in part by a surgical gown sleeve.

The surgical glove 30 comprises any suitable biocompatible material having the necessary properties disclosed herein. In one preferred embodiment, the material comprises latex. However, other natural, synthetic or combination materials are suitable as is known to those with skill in the art.

The inner surface of the hand portion 32 must fit the surgeon's hand closely to permit precise manipulation of tissues. The inner surface of the glove 30 can be provided with a lubricant, including powder to facilitate introduction of the surgeon's hand into the glove 30. The glove 30 can be provided in several thickness and in several sizes to accommodate the varying sizes of surgeons' hands.

Figures 3, 4:
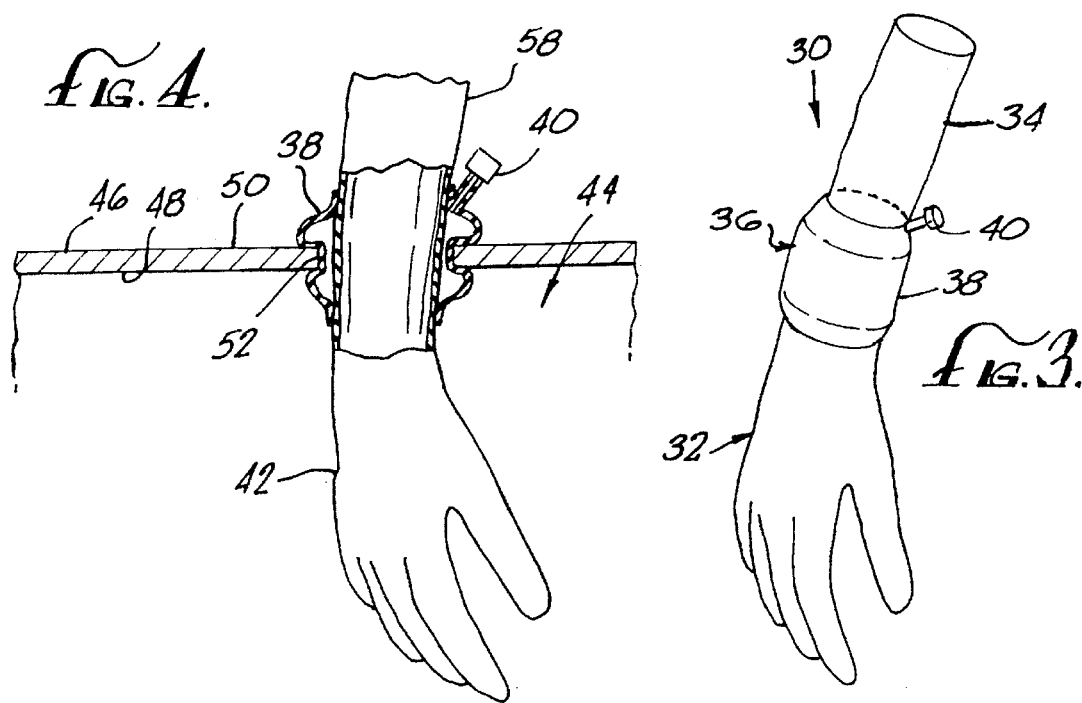
FIG. 3 is a perspective view of a surgical glove having features of the invention.
FIG. 4 is an environmental view of the surgical glove shown in FIG. 2 being used in surgery according to one embodiment of the present invention.

In the embodiment shown in FIGS. 3 and 4, the forearm portion 34 of the surgical glove 30 comprises a sealant 36 affixed thereto. In this embodiment, the sealant 36 comprises an inflatable cuff 38 circumferentially disposed around the forearm portion 34 of the glove 30, and having an inflation port 40 attached thereto. The circumferential cuff 38 comprises any appropriate, biocompatible material. Preferentially, the material is elastic though non-elastic material capable of being inflated can also be used. The inflation port 40 can be configured to permit entry of gas, such as air, or liquid such as sterile saline into the cuff 38 for inflation.

The cuff 38 can have a substantially constant thickness or can have different thickness in different areas of the cuff 38. For example, the cuff 38 can be thicker where attached to the forearm portion 34 of the glove 30 such that inflation preferentially occurs away from the forearm. This configuration has the advantage of being less likely to create a tourniquet effect around the forearm when the cuff 38 is inflated.

The size of the cuff 38 should be suitable for the use intended as disclosed herein. The uninflated cuff 38 preferentially has a low profile with respect to the forearm portion 34 of the glove 30. In the inflated state, the cuff 38 must have an axially thickness of sufficient dimensions to create the seal between the sides 52 of the opening and the forearm portion 34 of the glove 30. The axial thickness necessary will depend on the body habitus of the patient to some extent. In one preferred embodiment, the maximal axially thickness of the inflated cuff 38 is between 1 cm and 20 cm, however, larger axial thicknesses are within the scope of the invention. In a particularly preferred embodiment, the maximal axial thickness of the inflated cuff 38 is about 8 cm.

The external diameter of the inflated cuff 38 should be sufficient to create the seal according to the present invention. This maximum external diameter will vary with the size of the opening. In a preferred embodiment, the maximum external diameter of the inflated cuff 38 should be between about 5 cm and about 10 cm. In a particularly preferred embodiment, the maximum external diameter of the inflated cuff 38 should be about 7 cm.

Referring now to FIG. 4, there is illustrated an environmental view of the surgical glove 30 shown in FIG. 3 being used in surgery according to one embodiment of the present invention. As can be seen, the surgeon's gloved hand 42 has been inserted into the body cavity 44 through the body cavity wall 46 until the circumferential cuff 38 is approximately at the level of the body cavity wall 46.

Next, the cuff 38 is inflated through the inflation port 40 using an inflator such as a syringe, not shown. As the cuff 38 expands, it encounters the sides B2 of the opening, thereby creating a seal between the surgical glove 30 and the sides B2 of the opening. Though shown as overlapping the internal and external surfaces of the body cavity wall 46, the cuff 38 can rest entirely between the internal surface 48 and external surface B0 of the body cavity wall 46 for patients having a suitably thick body cavity wall 46. Preferably, the seal is substantially gas tight, such that a gas introduced under pressure into the body cavity 44 will does not leak out of the body cavity 44 between the sealant 36 and the sides B2 of the opening.

Referring now to FIGS. 5 and 6, there are illustrated perspective and environmental views respectively of another embodiment of a surgical glove 30 having a sealant 36 according to one aspect of the present invention. As disclosed above, the surgical glove 30 comprises a hand portion 32 and a forearm portion 34. In this embodiment, the sealant 36 comprises an inflatable cuff 38 having an inflation port 40 affixed thereto, and a flange S4. The sealant 36 can be affixed to the forearm portion 34 or can be detached from the forearm portion 34 of the glove 30 but having a central opening 56 for the glove 30 to slidably insert therein.

The size of the cuff 38 should be suitable for the use intended as disclosed herein. In the inflated state, as shown in FIGS. 5 and 6, the cuff 38 must have an axially thickness of sufficient dimensions to create the seal between the sides 52 of the opening and the forearm portion 34 of the glove 30. The axial thickness necessary will depend on the body habitus of the patient to some extent. In one preferred embodiment, the maximal axially thickness of the inflated cuff 38 is between 1 cm and 20 cm, however, larger axial thicknesses are within the scope of the invention. In a particularly preferred embodiment, the maximal axial thickness of the inflated cuff 38 is about 5 cm.

The external diameter of the inflated cuff 38 should be sufficient to create the seal according to the present invention. This maximum external diameter will vary with the size of the opening 22. In a preferred embodiment, the maximum external diameter of the inflated cuff 38 should be between about 5 cm and about 10 cm. In a particularly preferred embodiment, the maximum external diameter of the inflated cuff 38 should be about 7 cm. The internal diameter of the inflated cuff 38 should be larger than the maximum external diameter of the surgeon's gloved forearm 58 to permit axial movement of the surgeon's gloved hand 42 and forearm 58 though the center of the flange 54.

Referring now to FIG. 6, there is illustrated an environmental view of the surgical glove 30 shown in FIG. 5. In use, the surgeon inserts his hand in the glove 30. If the inflatable cuff 38 with flange 54 is detached from the forearm portion 34 of the glove 30, the surgeon places his gloved hand through the inflatable cuff 38 with flange 54, moving the cuff 38 to a position disposed circumferentially around the forearm portion 34 of the glove 30. The cuff 38 is preferentially not inflated during this insertion.

Next, the surgeon inserts his gloved hand 42 with the cuff 38 disposed around the forearm portion 34 of the glove 30 into the body cavity 44 through an opening in the body cavity wall 46. The inflatable cuff 38 is then inflated through the inflation port 40 by an inflator such as a syringe, not shown, until the cuff 38 contacts the sides 52 of the opening, thereby creating a substantially gas-tight seal. As can be seen in this embodiment, the provision of a flange 54 between the forearm portion 34 of the glove 30 and the inflation cuff 38 advantageously permits ease of movement of the surgeon's gloved hand within the body cavity 44 while maintaining the seal and avoiding a tourniquet effect around the surgeon's gloved forearm 58. Though shown as overlapping the internal surface 48 and external surface 50 of the body cavity wall 46, the cuff 38 can rest entirely between the internal surface 48 and external surface 50 of the body cavity wall 46 for patients having a suitably thick body cavity wall 46.

Referring now to FIGS. 7 and 8, there are illustrated perspective and environmental views, respectively, of a surgical glove 30 having a sealant 36 according to one embodiment of the present invention. As disclosed above, the surgical glove 30 comprises a hand portion 32 and a forearm portion 34. In this embodiment, the sealant 36 comprises a disk 60, having an distal layer 62 and a proximal layer 64, and a flange 54. The sealant 36 can be affixed to the forearm portion 34 of the glove 30 by the flange 54 or can be detached from the forearm portion 34 of the glove 30 but having a central opening 56 in the flange 54 for the glove 30 to slidably insert therein. The distal layer 62 comprises a biocompatible adhesive thereon. Suitable adhesives are well known in the surgical arts. The distal layer 62 further preferentially comprises a nonadhesive coat, not illustrated, with a removal mechanism 66, covering the adhesive distally. The proximal layer 64 preferably comprises substantially nonflexible material. The flange 54 preferably comprises substantially flexible material such as latex rubber.

The disk 60 can be substantially circular as shown or can be any other suitable shape including oval, square and rectangular. It should have dimensions large enough to cover the opening with the surgeon's gloved hand inserted therein. For example, a circular disk 60 having a 20 cm maximum diameter with a 5 cm horizontally thick adhesive coat can be used. Other dimensions are intended according to the present invention and can be selected by those with skill in the art with reference to the disclosure herein.

Referring now to FIG. 8, there is illustrated an environmental view of the surgical glove 30 shown in FIG. 7. In use, the surgeon inserts his hand in the glove 30. If the disk 60 with flange 54 is detachable from the forearm portion 34 of the glove 30, the surgeon places his gloved hand through the central opening 56 in the flange 54, moving the disk 60 to a position disposed circumferentially around the forearm portion 34 of the glove 30.

Once the surgeon's gloved hand is appropriately positioned within the body cavity 44, the nonadhesive coat is removed by the removal mechanism 66 thereby exposing the biocompatible adhesive. The distal layer 62 is then placed on the tissue surrounding the opening in the body cavity wall 46 or on a surgical covering placed on the tissue surrounding the opening in the body cavity wall 46, such as a sterile plastic film, not shown. As can be seen in FIG. 8, the provision of a flange 54 facilitates movement of the gloved surgeon's hand with respect to the body cavity wall 46. Though shown with a flange 54, the embodiment illustrated in FIG. 7 and 8 can be used without a flange 54 by having the disk 60 attach directly to the forearm portion 34 of the surgeon's gloved hand.

Referring now to FIGS. 9 and 10, there are illustrated perspective and environmental views of a surgical glove 30 having features of the present invention. In this embodiment, the invention comprises a surgical glove 30 having a hand portion 32 and a forearm portion 34 affixed to the hand portion 32 as disclosed above, in combination with a sealant 36. The sealant 36 comprises an inflatable cuff 38 having a central opening 56 therein and having an inflation port 40 affixed thereto. The cuff 38 has substantially the characteristics and dimensions disclosed above for the circumferentially cuff 38 illustrated in FIGS. 3 and 4.

In use, as shown in FIG. 10, the gloved surgeon's hand is placed through the central opening 56 of the inflation cuff 38 while the inflation cuff 38 is in the uninflated state. Second, the gloved surgeon's hand with the uninflated cuff 38 disposed around the forearm portion 34 of the glove 30 is passed through an opening in the body cavity wall 46 and the inflation cuff 38 aligned with the sides 52 of the opening 22. Next, the inflation cuff 38 is inflated through the inflation port 40 by an inflation mechanism such as a syringe, not illustrated, thereby creating a substantially gas-tight seal between the forearm portion 34 of the surgical glove 30 and the sides 52 of the opening. In this embodiment, movement of the surgeon's hand within the body cavity 44 is facilitated by the lack of a tight junction between the sealant 36 and the forearm portion 34 of the surgical glove 30.

As will be appreciated by those with skill in the art with reference to the disclosure herein, there are a variety of modifications and additions that can be incorporated into the sealant 36 disclosed herein, as contemplated by the present invention. For example, is an embodiment having a sealant 36 comprising an inflatable cuff 38, the cuff 38 can vary in the thickness and/or distensibility of the material in such a manner that it tends to expand preferentially at the sides 52 of the opening while putting less pressure on the forearm portion 34 of the surgeon's hand through the forearm portion 34 of the surgical glove 30.

Further, the shape of each of the sealant 36 disclosed and contemplated by the present invention can be substantially noncircular. For example, oval inflatable cuffs 38 can more appropriately seal some openings.

EXAMPLE I

CLINICAL COMPARISON BETWEEN LML SUBTOTAL COLECTOMY AND CONVENTIONAL OPEN SUBTOTAL COLECTOMY

Patient Selection:

I performed LML subtotal colectomies on 12 patients according to the present invention. None of these surgeries were converted to traditional open laparotomy. The patients consisted of 9 women and 3 men having ages between 40 and 80 years. Their average age was 68.9 years. Five of the patients had diagnoses of carcinoma, one of volvulus and six of diverticulitis.

A control group of 12 patients were randomly selected retrospectively from patients who underwent traditional open colectomies. The control group consisted of 7 women and 5 men having ages from 33 to 82. Their average age was 66.5 years. Five of the control patients had diagnoses of carcinoma, two of ulcerative coliris and three of diverticulitis. I performed two of the control surgeries. The remaining surgeries were performed by four other surgeons.

Surgical Technique:

I performed LML right hemicolectomies standing at the patient's left side. (I am right handed.) I initially made a 5 cm midline or left paramedian incision into the abdominal cavity. Next, I applied a 1-0 Vicryl® (Ethicon, Somerville, N.J.) suture in a figure-of-eight at each corner of this first opening. I inserted my gloved left hand and part of my left forearm through the first opening into the abdominal cavity and then used a trocar to make a second opening using my left hand intraperitoneally as a guide.

Next, I pulled the two figure-of-eight fascia sutures tightly around my forearm and clamped the sutures under tension with hemostats. This created a substantially gas-tight seal between the sides of the first opening and my left forearm.

I infused carbon dioxide gas through the second opening to a pressure of about 14 mmHG, adjusting the figure-of-eight sutures to maintain the seal as needed. Then, I inserted other trocars using a videoguide placed into the abdominal cavity though one of the openings as in conventional laparoscopy to create a total of two 10 mm openings and one 5 mm opening, in addition to the first opening. I introduced a 30 degree laparoscope through one of they 10 mm openings.

Using the videoguide, I used my right hand to manipulate curved Endoscissors® (Ethicon) with cautery and to assist in performing dissection though a 5 mm opening. I used my left hand inside the abdomen to perform the hemicolectomy in a manner substantially the same as in traditional, fully open laparotomy. That is, I used my left hand to palpate the lesion, to retract the colon and to bluntly dissect the retroperitoneum. Occasionally, I used a bowel clamp through one of the 10 mm openings to assist the soft tissue retraction of soft tissue.

Next, I introduced an Endoclip (Ethicon) through one of the 10 mm openings and used it to divide the vessels and omenrum as necessary. Once I freed the terminal ileum, cecum, ascending colon, proximal transverse colon and their mesentery from the surrounding tissue, I loosened the two sutures at the corners of the first opening by unclamping the hemostats and removed my left hand from the abdominal cavity. Then, I pulled the right colon and terminal ileum through the first opening and completed division of mesentery and bowel anastomosis extracorporeally as in open surgery. After replacing the anastomosed bowel back in the peritoneal cavity and closing the first opening, I performed laparoscopic examination to confirm hemostasis. Finally, I removed all remaining instrumentation from the abdominal cavity and closed the remaining openings in the usual manner.

I performed LML transverse hemicolectomies in a manner substantially similar to that disclosed herein for LML right hemicolectomies, with the following modifications. I stood on either side of the patient rather than only on the patient's left side. I placed the lower 10 mm openings at the lower midline.

I performed LML sigmoid colectomy in a substantially similar manner as disclosed above for LML right hemicolectomies, with the following modifications. I stood on the patient's right side. I made the first opening in the lower midline and I made the additional openings in the epigastric area and right upper and left lower quadrants of the abdomen.

Traditional colectomies on the control patients were performed using open laparotomy and techniques well known to those with skill in the art. All control surgeries were performed using staple techniques for bowel anastomosis.

Results:

The results of the LML hemicolectomies and control traditional open hemicolectomies are record in Table I.

TABLE I

Comparison of Results of 12 Patients Who Underwent Laparoscopic Mini Laparotomy Subtotal colectomy with A Control Group of 12 Patients Who Underwent Traditional Colectomy

|  | LML Colectomy (Averages) | Traditional Colectomy (Averages) |
|---|---|---|
| Operating time (min) | 135 | 100 |
| Shortest free margin of colon with carcinoma (cm) | 7 | 3.5 |
| Harvested lymph nodes in colon carcinoma | 9.1 | 8.2 |
| No. of IM analgesics | 4.5 | 8.4 |
| Postoperative days before starting oral intake | 2.0 | 3.3 |
| Length of stay (days) | 5.6 | 8.3 |

Morbidity was classified as major and minor. Major complications were those that prolonged inpatient hospital stays. Major complications included ileus, peritoneal abscess, and congestive heart failure. Minor complications were those that did not prolong inpatient hospital stays. Minor complications included wound, infection, atelectasis, diarrhea and urinary retention.

There were a total of two major complications (16 percent) in the 12 LML subtotal colectomies and three major complications (25 percent), including one death from congestive heart failure, in the 12 traditional open subtotal colectomies. Minor complications occurred in 4 (33 percent) of 12 LML subtotal colectomies and 5 (41 percent) of 12 traditional open subtotal colectomies. One patient who had LML subtotal colectomy developed an intermessenteric abscess which required an open laparotomy and drainage on the third postoperative day. The patient was discharged seven days after the second surgery. None of the complications, including the abscess, appeared to be directly related to the use of laparoscopic surgical techniques.

Although the present invention has been described in considerable detail with reference to certain preferred embodiments, other versions are possible. For example, a combination of sutures and a sealant, or combinations of sealants can be used to seal the sides of an opening in a body cavity wall to the forearm portion of a surgeon's glove. Therefore, the spirit and scope of the appended claims should not be limited to the description of the preferred embodiments disclosed herein.

I claim:

1. A method of performing surgery comprising the steps of:
   (a) making a first opening in a body cavity wall of a body cavity sufficient to permit entry of a surgeon's gloved hand into the body cavity, the first opening having sides and surrounding tissue;
   (b) placing the surgeon's gloved hand into the body cavity through the first opening;
   (c) suturing the sides of the first opening thereby creating substantially gas-tight seal between the sides of the first opening and the surgeon's gloved hand;
   (d) infusing a gas into the body cavity through the first opening or through a second opening in the body cavity wall;
   (e) performing a surgical procedure; and
   (f) removing the surgeon's hand from the body cavity.

2. The method of performing surgery of claim 1, wherein the body cavity is the abdomen.

3. The method of performing surgery of claim 1, wherein the first opening is an opening in the anterior abdominal wall.

4. The method of performing surgery of claim 1, wherein the surgery is laparoscopic-assisted mini laparotomy.

5. The method of performing surgery of claim 1, wherein the surgery is selected from the group consisting of a subtotal or total colectomy, splenectomy, prostatectomy, hepatectomy, pancreatectomy, nephrectomy, gastrectomy, abdominal exploration, cholecystectomy, esophageal and diaphragmatic surgery.

6. A method of performing surgery comprising the steps of:
   (a) providing a surgical glove and a sealant in combination; the surgical glove comprising a hand portion having an inner layer for closely engaging a surgeon's hand and a forearm portion attached to the hand portion, wherein the sealant is adapted to seal the forearm portion of the glove to sides or surrounding tissue of an opening in body cavity wall;
   (b) making a first opening in a body cavity wall of a body cavity sufficient to permit entry of a surgeon's gloved hand into the body cavity, the first opening having sides and surrounding tissue;
   (c) placing the surgeon's gloved hand into the body cavity through the first opening;
   (d) engaging or actuating the sealant to the sides or the surrounding tissue of the first opening, thereby creating a substantially gas-tight seal between the sides of the first opening and the forearm portion of the surgical glove;
   (e) infusing a gas into the body cavity through the first opening or through a second opening in the body cavity wall;
   (f) performing a surgical procedure; and
   (g) removing the surgeon's hand from the body cavity.

7. The method of performing surgery of claim 6, wherein the sealant in the providing step comprises an inflatable member having a central opening for permitting entry of a gloved surgeon's hand therethrough and having an inflation mechanism for inflating the inflatable member, and wherein the engaging step comprises inflating the sealant.

8. The method of claim 7, wherein the sealant in the providing step comprises a disk with a central opening having a proximal surface and a distal surface, the distal surface having an adhesive thereon, and wherein the engaging step comprises adhering the adhesive to the sides of the opening in the body cavity wall.

9. The method of performing surgery of claim 6, wherein the body cavity is the abdomen.

10. The method of performing surgery of claim 6, wherein the first opening is an opening in the anterior abdominal wall.

11. The method of performing surgery of claim 6, wherein the surgery is laparoscopic-assisted mini laparotomy.

12. The method of performing surgery of claim 6, wherein the surgery is selected from the group consisting of a subtotal or total colectomy, splenectomy, prostatectomy, hepatectomy, pancreatectomy, nephrectomy, gastrectomy, abdominal exploration, cholecystectomy, esophageal and diaphragmatic surgery.

13. A surgical glove and sealant in combination, the surgical glove comprising a hand portion having an inner surface for closely engaging a surgeon's hand and a forearm portion attached to the hand portion, wherein the sealant is adapted to seal the forearm portion of the glove to sides or surrounding tissue of an opening in a body cavity wall.

14. The combination of claim 13, wherein the sealant comprises an inflatable member having a central opening for permitting entry of a gloved surgeon's hand therethrough and having an inflation mechanism for inflating the inflatable member.

15. The combination of claim 14, wherein sealant further comprises a flange having a central opening disposed within the central opening of the inflatable member and affixed to the inflatable member.

16. The combination of claim 15, wherein the flange is is affixed to the forearm portion of the surgical glove.

17. The combination of claim 13, wherein the sealant comprises a disk with a central opening having a proximal surface and a distal surface, the distal surface having an adhesive thereon.

18. The combination of claim 17, wherein the sealant further comprises a flange having a central opening disposed within the central opening of the disk and affixed to the inflatable member.

19. The combination of claim 18, wherein the flange is affixed to the forearm portion of the surgical glove.

* * * * *